United States Patent [19]

Pettersen et al.

[11] Patent Number: 5,393,741
[45] Date of Patent: Feb. 28, 1995

[54] ACETAL DERIVATIVES OF AROMATIC ALDEHYDES

[75] Inventors: Erik O. Pettersen, Oslo; Rolf O. Larsen, Langesund; Bernt Borretzen, Porsgrunn; John M. Dornish, Bekkestua; Reidar Oftebro, Hvalstad, all of Norway

[73] Assignee: Norsk Hydro a.s., Oslo, Norway

[21] Appl. No.: 799,070

[22] Filed: Nov. 27, 1991

[30] Foreign Application Priority Data

Nov. 30, 1990 [GB] United Kingdom ............... 9026114

[51] Int. Cl.⁶ ................... A61K 31/34; A61K 31/335
[52] U.S. Cl. ............................. 514/23; 536/1.11; 536/18.7; 544/53; 549/315
[58] Field of Search ................. 536/1.1, 18.7, 1.11; 514/23; 544/53; 549/315

[56] References Cited

U.S. PATENT DOCUMENTS

| | | | |
|---|---|---|---|
| 3,925,487 | 12/1975 | Borretzen et al. | 558/24 |
| 4,395,406 | 7/1983 | Gacek et al. | 536/23 |
| 4,723,986 | 2/1988 | Teach | 71/88 |
| 4,874,780 | 10/1989 | Borretzen et al. | 514/471 |
| 5,032,610 | 7/1991 | Borretzen et al. | 514/474 |
| 5,049,396 | 9/1991 | Oftebro et al. | 424/649 |
| 5,135,948 | 8/1992 | Borretzen et al. | 514/467 |
| 5,149,820 | 9/1992 | Borretzen et al. | 548/215 |

FOREIGN PATENT DOCUMENTS

| | | |
|---|---|---|
| 0085760 | 8/1983 | European Pat. Off. |
| 57-88170 | 6/1982 | Japan. |
| 2177089 | 1/1987 | United Kingdom. |

OTHER PUBLICATIONS

Gardella, J. E., et al., *Biochemical and Biophysical Research Communications*, vol. 173, No. 3, 1990; pp. 1292–1298.
Bowie et al., *Chemical Abstracts*, vol. 79, No. 17, 104472c (Oct. 29, 1973).
Lezina et al., *Chemical Abstracts*, vol. 85, No. 11, 85:77389w (Sep. 13, 1976).
Raey-Maekers et al., *Chemical Abstracts*, vol. 87, No. 21, 87:168033h (Nov. 21, 1977).
Makosza et al., *Chemical Abstracts*, vol. 100, No. 21, 100:174365w (May 21, 1984).
Makosza et al., *Chemical Abstracts*, vol. 101, No. 25, 101:230059j (Dec. 17, 1984).
Asahi Chemical Industry Co., Ltd., *Chemical Abstracts*, vol. 102, No. 7, 102:62213e (Feb. 18, 1985).
Cooper et al., *Chemical Abstracts*, vol. 112, No. 17, 112:158022z (Apr. 23, 1990).
Katakami et al., *Chemical Abstracts*, vol. 115, No. 3, 115:29363z (Jul. 22, 1991).
*Chemical Abstracts*, 110:94465v, 110(11) (1989).
*Chemical Abstracts*, 108:93846s, 108(11) (1988).
*Chemical Abstracts*, 104:207215k, 104(23) (1986).
*Chemical Abstracts*, 15157r, 78(3) (1973).
*Chemical Abstracts*, 113705f, 68(25) (1968).

*Primary Examiner*—Ronald W. Griffin
*Attorney, Agent, or Firm*—Wenderoth, Lind & Ponack

[57] ABSTRACT

New compounds having the general formula I

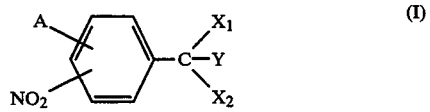

wherein Y may be H or D;
and A is H, D, alkyl with 1–4 C-atoms, halogen, nitro, amino, monoalkyl amino or dialkyl amino wherein the alkyl groups have 1–4 C atoms or OR wherein R is H or alkyl of 1–4 C-atoms;
$X_1$ and $X_2$ may together with the carbon atom to which they are bound form a cyclic acetal, thioacetal, dithiane, aminal, oxazolidine or thiazolidine;
or pharmaceutically acceptable salts thereof.

The compounds are useful as anti-carcinoma agents.

5 Claims, No Drawings

ACETAL DERIVATIVES OF AROMATIC ALDEHYDES

The present invention concerns new compounds which may be used in the treatment of patients afflicted with carcinoma. The compounds according to the present invention are acetal derivatives of aromatic aldehydes, which carry a nitro group on the phenyl group of the benzylidene moiety.

TECHNICAL FIELD

It is known from, among others, EP215395, J63264411, J88009490, J55069510 and EP283139 that benzaldehydes and acetals thereof have an anti-cancer effect. These compounds exert an inhibitory action on the protein synthesis of the cells.

In solid tumours this reduced protein synthesis may result in a lack of vital proteins which lead to cell death. In normal cells there is a potential capacity for protein synthesis which is higher than in most cancer cells of solid tumours. This is demonstrated by comparison of the cell cycle duration in normal stem cells, which is often below 10 h, and that of most cancer cells of solid tumours, which is typically 30–150 h (see Gavosto and Pileri in: *The Cell Cycle and Cancer.* Ed. :Baserga, Marcel Dekker Inc., N.Y. 1971, pp 99). Since cells, as an average, double their protein during a cells cycle, this means that protein accumulation is higher in growth-stimulated normal cells than in most types of cancer cells.

Keeping in mind this difference between normal and cancer cells, there is another difference of similar importance: while normal cells respond to growth-regulatory stimuli, cancer cells have a reduced or no such response. Thus, while normal cells, under ordinary growth conditions, may have a reserve growth potential, cancer cells have little or no such reserve. If a mild protein synthesis inhibition is imposed continuously over a long period of time on normal cells as well as on cancer cells it is probable that the two different types of cells will respond differently: Normal tissue may take into use some of its reserve growth potential and thereby maintain normal cell production. Cancer tissue however, have little or no such reserve. At the same time the rate of protein accumulation in most cancer cells is rather low (i.e. protein synthesis is only a little greater than protein degradation). Therefore the mild protein synthesis inhibition may be just enough to render the tumour tissue imbalanced with respect to protein accumulation, giving as a result a negative balance for certain proteins. During continuous treatment for several days this will result in cell inactivation and necrosis in the tumour tissue while normal tissue is unharmed.

In EP283139 it was reported that the substitution of the aldehyde hydrogen with a deuterium in the benzylidene moiety leads to an even stronger inhibition of the protein synthesis. Further, it was reported that those new acetals had a longer half life in the cells.

It has now surprisingly been found that the introduction of a nitro group as substituent on the phenyl group in such compounds gives a stronger inhibition of the protein synthesis, especially at higher concentrations.

DETAILED DESCRIPTION

The compounds of the present invention have the general formula:

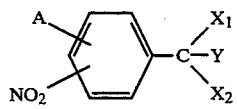

wherein Y may be H or D;

and A is H, D, or alkyl with 1–4 C-atoms, halogen, nitro, amino, monoalkyl amino or dialkyl amino wherein the alkyl groups have 1–4 C atoms, or OR wherein R may be H or alkyl with 1–4 C-atoms;

$X_1$ and $X_2$ may together with the carbon atom to which they are bound form a cyclic acetal, thioacetal, dithiane, aminal, oxazolidine or thiazolidine;

and pharmaceutically acceptable salts thereof.

The phenyl ring of the compounds of formula I may carry one or several groups A, at the most four A groups. It is most preferred when there are several A groups present that these groups are the same or that at least one of them is a further nitro group.

When A is deuterium this means that the phenyl ring may be partly or fully deuterated, carrying at the most four deuterium atoms on the phenyl ring.

When A is alkyl it is most preferred to be methyl or ethyl.

The halogens may be any of chlorine, bromine, iodine or fluorine.

The pharmaceutical acceptable salts may be alkali metal salts, such as sodium salts, alkali earth metal salts, such as magnesium or calcium salts, ammonium salts, salts with organic aminobases or the like.

The nitro group may be in the positions 2, 3 or 4 for compounds of formula I wherein A is H, but the most preferred position is number 3. These compounds may be represented by the following general formula II:

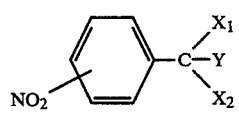

In compounds of formula I, wherein A is not H, the nitro group may be in any of the 2, 3, 4, 5 or 6 positions and the choice of position may be achieved through the position of the substituent A.

When A is nitro or there are more than one substituent A, one of which is an additional nitro group, most preferred positions for the two nitro groups will be in the 2 and 6 positions or the 3 and 5 positions depending on the position and influence of the other substituent A.

Particularly useful sub-classes of compounds of this invention are represented by formulae III–V below:

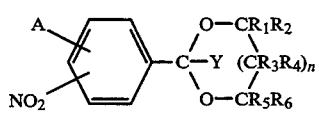

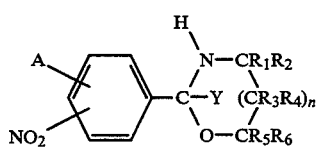

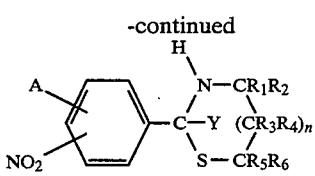

wherein:
Y and A are as defined above,
n is 0 or 1,
R₁, R₂, R₃, R₄, R₅ and R₆ may be H, OH, alkyl with 1-4 carbon atoms, which may be unsubstituted or substituted, phenyl which may be unsubstituted or substituted, or a heterocycle or a sugar molecule which may be substituted or unsubstituted;
or R₁ and R₃ or R₃ and R₅ may together with the C atoms to which they are bound form a sugar molecule or a heterocycle;
or a pharmaceutically acceptable salt of said compounds.

In formulae III-V, the said further substitutions at one or several carbon atoms are, for example, preferably an OH group, a sugar molecule or a heterocycle.

Within the sub-class represented by formula III above there may be especially mentioned the compounds represented by formulae IIIa, IIIaa and IIIab below:

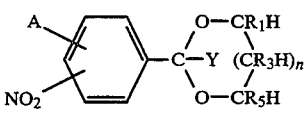

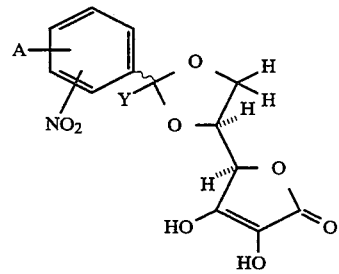

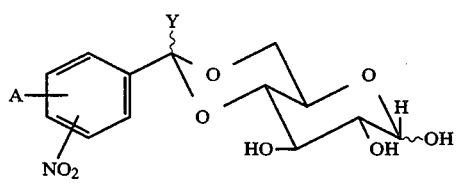

wherein:
Y and A are as defined above,
n is 0 or 1,
R₁ and R₃ or R₃ and R₅ may together with the C atom to which they are bound form a sugar molecule or a heterocycle; or
a pharmaceutically acceptable salt of said compounds.

PREPARATION

The cyclic derivatives of the present invention may be prepared by well-known processes for preparing cyclic acetals from aldehydes such as reacting nitro-benzaldehydes or lower acetals thereof with a di-or polyhydric alcohol in the presence of an acidic catalyst. These reactions may conveniently be carried out in a dipolar solvent such as dimethyl formamide, dimethyl sulphoxide, dimethyl acetamide or the like. Similarly, the preparation of the oxazolidines, aminals, oxathiolanes, dithianes and thiazolidines proceeds in a conventional manner by reacting the nitro-benzaldehyde, which may be further substituted, with the corresponding aminoalcohols, diamines, thioalcohols, dithiols and thioamines respectively.

These reactions are carried out in solvents which form an azeotropic mixture with the water formed in the reaction. Typical solvents used are inert hydrocarbons, preferentially benzene or toluene, which are capable by azeotropically removing the water formed, to drive the reaction to a completion.

The reaction conditions and solvents used will in each individual reaction depend on the reactivity and solubility of the reactants.

Generally the compounds according to the present invention may be prepared as shown below in the reaction scheme for the preparation of substituted benzylidene ascorbic acid acetals wherein R is nitro:

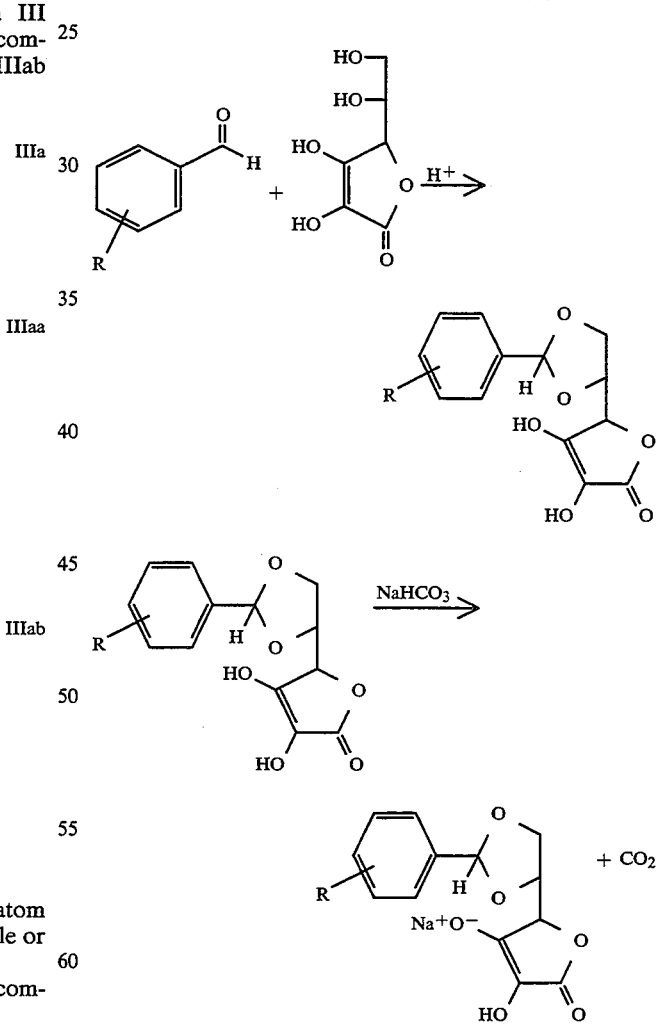

The compounds of formula I wherein Y is deuterium may be prepared as described above, but starting with deuterated nitro-benzaldehydes, which may carry one or more further substituents on the phenyl ring, or lower acetals thereof.

The following examples are illustrative for how the compounds of the present invention may be prepared.

EXAMPLE 1

Preparation of sodium-5,6-(3-nitro)-benzylidene-L-ascorbate-$d_1$

Step 1: Preparation of 3-Nitro-benzaldehyde-$d_1$

Benzaldehyde-$d_1$ (60 ml, 0.58 moles) was added dropwise to an ice-cooled, mechanically stirred mixture of fuming nitric acid (21.5 ml, 0.51 moles) and sulphuric acid (250 ml). The temperature was not allowed to rise above 5° C. When the addition was completed, the reaction mixture was heated to 40° C., then allowed to reach room temperature. By slowly pouring the mixture on crushed ice, pale yellow crystals were immediately formed. These were collected by filtering on a glass sintered funnel and washed with water. Thereafter they were dissolved in toluene and washed with a 10% $NaHCO_3$ solution. After drying with $MgSO_4$, the crude product was distilled under vacuum to give a pale yellow solid, mp 53°–55° C.

Yield: 37.6 g, 48% of theory. The purity was shown to be 93% (GC), the main impurity being the o-isomer. The degree of deuteration was 99.8% according to NMR.

Step 2: Preparation of sodium-5,6-(3-nitro)-benzylidene-L-ascorbate-$d_1$ 3-nitro-benzaldehyde-$d_1$ (27.7 g, 0.182 moles) and L-ascorbic acid (32.0 g, 0.182 moles) were dissolved in dry dimethylforamide (130 ml) in a 500 ml three-necked flask. Conc. sulfuric acid (1.5 ml) was carefully added and the reaction mixture was stirred at room temperature for 24 hours.

The reaction was continued for 2 days by evaporating at 35°–40° C. at the vacuum obtained at a water jet. By changing to an oil pump and evaporating for another 2 days, the solvent was removed. A solution of $NaHCO_3$ (18.5 g, 0.22 mol) in degassed water (150 ml) was added to the viscous residue, whereby the pH was raised to 6. This solution was evaporated over night and the crude product purified on a prepacked reverse phase column (Lobar C), while eluting with 5% methanol/water. Freeze drying the product fractions gave the title compound as a brown solid. Yield: 30%.

The structure was confirmed by $^1H$ NMR and the degree of deuteration was shown to be 99.5%.

EXAMPLE 2

Sodium 5,6-(3-nitro)-benzylidene-L-ascorbate

In a 100 ml glass reactor, 5 g (0.033 moles) of 3-nitrobenzaldehyde and 5.8 g (0.033 moles) of L-ascorbic acid were dissolved in 30 ml dry dimethylformamide (DMF). The reaction was started by slowly adding 0.5 ml conc. sulphuric acid. The reaction was performed with stirring under an inert atmosphere ($N_2$) at room temperature for 100 h.

The reaction mixture was then evaporated under high vacuum at a temperature of maximum 40° C. During evaporation the reaction goes further to completion as shown by the GLC analysis of the trimethylsilyl ethers. After most of the DMF has been removed, (>90%), the raw product was neutralized with 2.7 g sodium bicarbonate in 25 ml water. After the $CO_2$ evolution had ceased, the solution was evaporated under high vacuum (<2 mBar) at max. 40° C.

The product was further purified by preparative HPLC on a RP-18 column to remove unreacted starting materials.

The yield of the final product sodium 5,6-(3-nitro)-benzylidene-L-ascorbate is 11 g (40%).

GC-MS of the trimethylsilylether showed the molecular ion at m/e453, which confirmed the proposed structure. The structure was further confirmed by $^1H$-NMR spectroscopy at 300.13 MHz.

Biological experiments

In the following in vitro experiments, the rate of protein synthesis was measured for a compound from the prior art, which is deuterated sodium 5,6-O-benzylidene-L-ascorbate (Zilascorb($^2H$)), and for two compounds according to the present invention, sodium 5,6-(3-Nitro)-benzylidene-ascorbate (Nitro-BASS) and deuterated sodium 5,6-(3-Nitro)-benzylidene-ascorbate (Nitro-BASS-$d_1$)

Cell Culturing Techniques and Synchronization

Human cells of the established line NHIK 3025, originating from a cervical carcinoma in situ (Nordbye, K. and Oftebro, R., Exp. Cell Res., 58: 458, 1969), Oftebro, R. and Nordbye, K., Exp. Cell Res., 58: 459–460, 1969) were cultivated in medium E2a (Puck et al., J. Exp. Med., 106: 145–165, 1957) supplemented with 20% human (prepared at the laboratory) and 10% horse serum (Grand Island Biological Co.).

The cells are routinely grown as monolayers in tissue culture flasks. The cells were kept in continuous exponential growth by frequent reculturing, i.e. every second and third day, and were obtained by repeated selection of mitotic cells (Pettersen et al., Cell Tissue Kinet., 10: 511–522, 1977). During reculturing as well as during experiments the cells were kept in a walk-in incubator at 37° C. Under growth conditions as used here, the NHIK 3025 cells have a medium cell-cycle time of ~18 hr, with medium $G_1$, $S_1$ and $G_2$ durations of ~7, ~8 and ~2.5 hr, respectively.

Protein Synthesis

The rate of protein synthesis was calculated as described previously (Ronning et al., J. Cell Physiol., 107: 47–57, 1981). Briefly, cellular protein was labeled to saturation during a 2-day preincubation with [$^{14}C$]valine of constant specific radioactivity (0.5 Ci/mol) prior to the experiment. This was achieved by using a high concentration of valine so that the dilution of [$^{14}C$]valine by intracellular valine and by proteolytically generated valine will be negligible (Ronning et al., Exper. Cell Res., 123: 63–72, 1979), thus keeping the specific radioactivity at a constant level. The rate of protein synthesis was calculated from the incorporation of [$^3H$]valine of constant specific activity. The incorporated measurements were related to the total of [$^{14}C$] radioactivity in protein at the beginning of the respective measurement periods and expressed as the percentage per hr (Ronning et al., J. Cell. Physiol., 107: 47–57, 1981).

Results

The protein synthesis inhibition induced by Zilascorb($^2H$), Nitro-BASS and Nitro-BASS-$d_1$ was measured in human NHIK 3025 cells after administration of the compounds at a concentration of 10 mM. In table 1 the rate of protein synthesis is given in per cent relative to an untreated control. The values presented represent one experiment, and are a mean of 3 samples±standard error.

TABLE 1

Rate of protein synthesis relative to an untreated control:

| DRUG | FORMULA | RATE OF PROTEIN SYNTHESIS (%) |
|---|---|---|
| Zilascorb ($^2$H) | 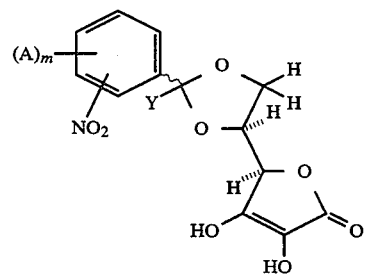 | 30.1 ± 0.8 |
| Nitro-BASS | 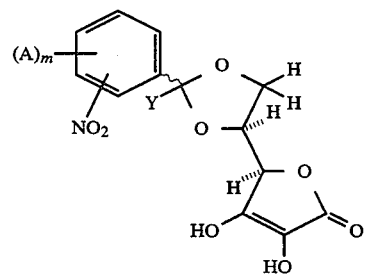 | 24.0 ± 0.3 |
| Nitro-BASS-d$_1$ | 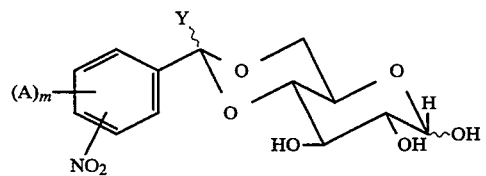 | 15.6 ± 0.9 |

Several other experiments have shown the same type of effect.

According to present invention the compounds of formula I may be administered to a patient in need of anti-carcinoma treatment.

For this purpose the compounds may be formulated in any suitable manner for administration to a patient either alone or in admixture with suitable pharmaceutical carriers or adjuvants.

It is especially preferred to prepare the formulations for systemic therapy either as oral preparations or parenteral formulations.

Suitable enteral preparations will be tablets, capsules, e.g. soft or hard gelatine capsules, granules, grains or powders, syrups, suspensions, solutions or suppositories. Such will be prepared as known in the art by mixing one or more of the compounds of formula I with non-toxic, inert, solid or liquid carriers.

Suitable parental preparations of the compounds of formula I are injection or infusion solution.

The preparations can contain inert or pharmacodynamically active additives. Tablets or granulates e.g. can contain a series of binding agents, filler materials, carrier substances and/or diluents. Liquid preparations may be present, for example, in the form of a sterile solution. Capsules can contain a filler material or thickening agent in addition to the active ingredient. Furthermore, flavour-improving additives as well as the substances usually used as preserving, stabilizing, moisture-retaining and emulsifying agents, salts for varying the osmotic pressure, buffers and other additives may also be present.

The dosages in which the preparations are administrered can vary according to the mode of use and the route of administration, as well as to the requirements of the patient. In general a daily dosage for a systemic therapy for an adult average patient will be about 1–500 mg/kg body weight/day, preferably 20–200mg/kg body weight/day.

The proportion of active ingredient in the pharmaceutical composition will vary depending upon the type of preparation but may generally be within the range of approximately 0.1 to 20% by weight for oral administration and for absorption through mucous membranes, and about 0.01 to 10% by weight for parenteral administration.

If desired the pharmaceutical preparation of the compound of formula I can contain an antioxidant, e.r. tocopherol, N-methyl-tocopheramine, butylated hydroxyanisole, ascorbic acid or butylated hydroxytoluene.

We claim:

1. A compound of formula IIIa, IIIaa or IIIab:

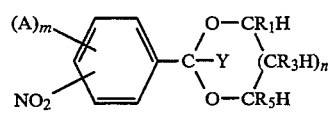

IIIa

IIIaa

IIIab wherein:
Y is H or D;
A is H, D, alkyl with 1–4 C-atoms, halogen, nitro, amino, monoalkylamino or dialkylamino wherein the alkyl groups have 1–4 C atoms, or OR wherein R is H or alkyl of 1–4 C-atoms;
n is 0 or 1;
m is an integer of 1–4; and
either $R_1$ and $R_3$ together with the C atoms to which they are bound form a sugar molecule and $R_5$ is H, OH, alkyl with 1–4 carbon atoms which may be unsubstituted or substituted or phenyl which may be unsubstituted or substituted, or $R_3$, and $R_5$ together with the C atoms to which they are bound form a sugar molecule and $R_1$ is H, OH, alkyl with 1–4 carbon atoms Which may be unsubstituted or substituted or phenyl which may be unsubstituted or substituted;
or a pharmaceutically acceptable salt thereof.

2. A compound according to claim 1, namely 5,6-(3-nitro)-benzylidene-L-ascorbic acid or a pharmaceutically acceptable salt thereof.

3. A compound according to claim 1, namely 5,6-(3-nitro)-benzylidene-L-ascorbic acid-$d_1$ or a pharmaceutically acceptable salt thereof.

4. A pharmaceutical composition comprising (1) a therapeutically effective amount of a compound according to claim 1, 2 or 3, and (2) a pharmaceutically acceptable carrier or diluent therefor.

5. A method for treating a patient afflicted with carcinoma which comprises administering to said patient a therapeutically effective amount of a compound according to claim 1, 2 or 3.

* * * * *